United States Patent
Xu et al.

(10) Patent No.: US 11,551,029 B2
(45) Date of Patent: Jan. 10, 2023

(54) DEEP NETWORK LUNG TEXTURE RECOGNITON METHOD COMBINED WITH MULTI-SCALE ATTENTION

(71) Applicant: DALIAN UNIVERSITY OF TECHNOLOGY, Liaoning (CN)

(72) Inventors: Rui Xu, Liaoning (CN); Xinchen Ye, Liaoning (CN); Haojie Li, Liaoning (CN); Lin Lin, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 249 days.

(21) Appl. No.: 17/112,367

(22) Filed: Dec. 4, 2020

(65) Prior Publication Data
US 2021/0390338 A1 Dec. 16, 2021

(30) Foreign Application Priority Data
Jun. 15, 2020 (CN) .......................... 202010541939.4

(51) Int. Cl.
*G06K 9/00* (2022.01)
*G06K 9/62* (2022.01)
(Continued)

(52) U.S. Cl.
CPC ......... *G06K 9/6251* (2013.01); *G06K 9/6256* (2013.01); *G06K 9/6262* (2013.01);
(Continued)

(58) Field of Classification Search
CPC .. G06K 9/6251; G06K 9/6256; G06K 9/6262; G06N 3/08; G06N 3/0481; G06N 3/0454; G06V 10/30; G06V 2201/031; G06V 10/776; G06V 10/82; G16H 30/40; G16H 50/20; G06T 7/41;
(Continued)

(56) References Cited

FOREIGN PATENT DOCUMENTS

| CN | 110570431 A | * | 12/2019 | |
| CN | 110674866 A | * | 1/2020 | ............ A61B 6/502 |
| WO | WO-2020093042 A1 | * | 5/2020 | |

OTHER PUBLICATIONS

R. Xu, Y. Hirano, R. Tachibana, and S. Kido, "Classification of diffuse lung disease patterns on high-resolution computed tomography by a bag of words approach," in International Conference on Medical Image Computing & Computer-assisted Intervention (MICCAI), 2011, pp. 183-190.

(Continued)

*Primary Examiner* — Xin Jia
(74) *Attorney, Agent, or Firm* — Muncy, Geissler, Olds & Lowe, P.C.

(57) ABSTRACT

The invention discloses a deep network lung texture recognition method combined with multi-scale attention, which belongs to the field of image processing and computer vision. In order to accurately recognize the typical texture of diffuse lung disease in computed tomography (CT) images of the lung, a unique attention mechanism module and multi-scale feature fusion module were designed to construct a deep convolutional neural network combing multi-scale and attention, which achieves high-precision automatic recognition of typical textures of diffuse lung diseases. In addition, the proposed network structure is clear, easy to construct, and easy to implement.

2 Claims, 3 Drawing Sheets

(51) Int. Cl.
   G16H 50/20    (2018.01)
   G16H 30/40    (2018.01)
   G06N 3/08     (2006.01)
   G06V 10/30    (2022.01)

(52) U.S. Cl.
   CPC ............ *G06N 3/08* (2013.01); *G06V 10/30* (2022.01); *G16H 30/40* (2018.01); *G16H 50/20* (2018.01); *G06V 2201/031* (2022.01)

(58) Field of Classification Search
   CPC . G06T 2207/10081; G06T 2207/20081; G06T 2207/20084; G06T 2207/30061
   See application file for complete search history.

(56) References Cited

OTHER PUBLICATIONS

M. Anthimopoulos, S. Christodoulidis, and et. al., "Lung pattern classification for interstitial lung diseases using a deep convolutional neural network," IEEE Transactions on Medical Imaging, 2016, pp. 1207-1216, vol. 35, No. 5.

Kaiming He, Xiangyu Zhang, and et al., "Deep residual learning for image recognition," in *Computer Vision and Pattern Recognition*, 2016, pp. 770-778.

K. Simonyan and A. Zisserman, "Very deep convolutional networks for large-scale image recognition", ICLR, 2015, 14 pages.

K. He and et al., "Identity mappings in deep residual networks," in European Conference on Computer Vision, 2016, pp. 630-645.

Y. Lecun, L. Bottou, Y. Bengio, and P. Haffner, "Gradient-based learning applied to document recognition," Proceedings of the IEEE, vol. 86, No. 11, pp. 2278-2324, 1998.

R. Xu and et al., "Pulmonary textures classification using a deep neural network with appearance and geometry cues," in IEEE International Conference on Acoustics, Speech and Signal Processing (ICASSP), 2018, 1 page.

* cited by examiner

DEEP NETWORK LUNG TEXTURE RECOGNITON METHOD COMBINED WITH MULTI-SCALE ATTENTION

TECHNICAL FIELD

The invention belongs to the fields of medical image processing and computer vision, and particularly relates to a deep network lung texture recognition method combined with multi-scale attention.

BACKGROUND

Diffuse lung disease refers to the general term for abnormal texture of the lung interstitial caused by factors such as inflammation or injury in the lung area. Because CT images can clearly show the status of lung tissue, they are often used to detect such diseases. However, due to the large number of images collected and the complicated lung texture, it is difficult for even experienced radiologists to accurately identify different types of lung texture, causing misdiagnosis. Therefore, it is necessary to establish a Computer Aided Diagnosis (CAD) system to assist radiologists to diagnose lung texture in CT images accurately and efficiently. A key technology for establishing this CAD system is to accurately and efficiently identify the lung texture contained in any region of interest in the lung region of the CT image.

The traditional CT image lung texture recognition method is usually based on a two-step method, that is, first, manually design features that can characterize lung texture characteristics, and then train a classifier that can effectively distinguish these features. Because the training classifier technology is relatively mature, researchers are more concerned about how to design more representative features, such as a bag-of-feature-based lung texture recognition method (R. Xu, Y. Hirano, R. Tachibana, and S. Kido, "Classification of diffuse lung disease patterns on high-resolution computed tomography by a bag of words approach," in International Conference on Medical Image Computing & Computer-assisted Intervention (MICCAI), 2011, p. 183.). However, the limited representation capability of artificially designed features makes the recognition accuracy of these recognition methods greatly different from the requirements of CAD systems.

In recent years, deep neural networks have brought a revolutionary impact in the field of image processing. This technology has also been used in lung texture recognition, such as a classification of lung texture based on convolutional neural network (CNN) (M. Anthimopoulos, S. Christodoulidis, and et. al., "Lung pattern classification for interstitial lung diseases using a deep convolutional neural network," IEEE Transactions on Medical Imaging, vol. 35, no. 5, pp. 1207-1216, 2016). Most of these methods use conventional stacked CNN structures or use CNN structures originally used for other image processing tasks (such as natural image recognition) for transfer learning, and have not yet fully and directly exerted the performance of CNN on lung texture recognition tasks. Although the recognition accuracy of the method based on the deep neural network is improved compared with the traditional method, it still has a gap with the required accuracy of the CAD system.

The above method has the following two problems. First, the lung texture in CT images presents two radiological features, grayscale and scale information. Currently, most CNNs used for lung texture recognition only use grayscale feature information, and have not focused on learning the scale features contained in the lung texture. Therefore, it is necessary to design and use a mechanism to enable CNN to learn multi-scale feature information of lung texture. Second, the current CNN parameters used for lung texture recognition are generally large, the feature maps learned by the CNN have redundant information, which affects the final recognition accuracy. It is necessary to design and use a mechanism to automatically filter feature maps that are beneficial for the recognition task, and automatically suppress the feature maps with weaker relationship with the recognition task to reduce the impact of redundant information in the feature maps and improve the final recognition accuracy.

SUMMARY OF THE INVENTION

The present invention aims to overcome the shortcomings of the prior art, and provides a deep network lung texture recognition method combined with multi-scale attention. This method uses a convolution module to build a basic network, a multi-scale feature fusion module to learn multi-scale feature information of lung texture, and an attention mechanism module to automatically filter features that are beneficial to the recognition task while suppressing features with weaker relationships with recognition task to achieve high-precision automatic recognition of lung texture.

The specific technical solution of the present invention is a deep network lung texture recognition method combined with multi-scale attention, including the following steps:

1) Initial data preparation: The initial data includes lung texture CT image patches and corresponding class labels for training and testing.

2) Recognition network construction: use the convolution and residual modules to construct the basic network, use the multi-scale feature fusion module to learn the multi-scale feature information of the lung texture, and use the attention mechanism module to automatically filter the feature maps, and ultimately improve the recognition accuracy.

3) Recognition network training: Train based on the recognition network obtained in step (2).

4) Use test data to evaluate network performance.

The recognition network construction includes the following steps:

2-1) The recognition network is composed of basic network, attention mechanism module and multi-scale feature fusion module. The basic network learns the feature information from the input CT lung texture image patches at different scales; The feature information learned at each scale automatically filters the feature information that is beneficial to the recognition task through the attention mechanism module, and automatically suppresses the feature information with weaker relationship with the recognition task; The feature information learned at different scales is finally fused by the multi-scale feature fusion module, and the recognition results are given;

2-2) The network contains several convolution modules. Each convolution module is composed of general units of deep neural network, that is, convolution layer, batch normalization layer, and rectified linear unit layer; The convolution modules are connected by jump connections to form several residual modules, which improves the efficiency of feature learning by introducing residual learning mechanism;

2-3) The network contains several attention mechanism modules, which are used to automatically filter the feature information that is beneficial to the recognition task from the feature information learned by the convolution module or the residual module, and automatically suppress the feature information that is weakly related to the recognition task;

2-4) The feature information learned by the network at different scales is effectively fused through the multi-scale feature fusion module, and the recognition results are given;

Recognition network training includes the following steps:

3-1) Online data augmentation is performed on the CT image patches participating in the training, and the specific forms include random flipping and random translation.

3-2) The recognition network is trained in small batches, use the classification cross-entropy loss function, and the loss function formula is as follows:

$$L(y, y') = -\frac{1}{n}\sum_{x}(y'\log(y))$$

In the formula, L(·) represents the value of the classification cross-entropy loss function, n represents the number of CT image patches participating in training in a single batch, x represents the data matrix of CT image patches participating in training in a single batch, and Σ is the summation operator, Y' represents the category label matrix corresponding to x, log(·) represents the logarithmic operation, and y represents the category label matrix of x recognized by the recognition network.

3-3) Through the stochastic gradient descent algorithm, use the loss function in step (3-2) to optimize the recognition network The beneficial effects of the present invention are:

The present invention is a deep network lung texture recognition method combined with multi-scale attention, using convolution and residual modules to construct a basic network, and learning multi-scale feature information from input CT lung texture image patches at three different scales. Use the attention mechanism module to automatically filter the feature information that is beneficial to the recognition task, and at the same time suppress the feature information that is weakly related to the recognition task. The multi-scale feature fusion module is used to fuse feature information of three scales and give a recognition result with higher correct recognition accuracy. The system has the following characteristics:

1. The system is easy to construct, and the recognition network only needs CT lung texture image patches as input to obtain a recognition result with higher recognition accuracy;

2. The program is simple and easy to implement;

3. The attention mechanism module can automatically filter the feature information that is beneficial to the recognition task, and at the same time automatically suppress the feature information that is weakly related to the recognition task to improve the recognition accuracy;

4. The multi-scale feature fusion module can effectively fuse the multi-scale feature information learned at each scale of the recognition network, and comprehensively give a recognition result with higher recognition accuracy.

BRIEF DESCRIPTION

DETAILED DESCRIPTION

Figure 1:
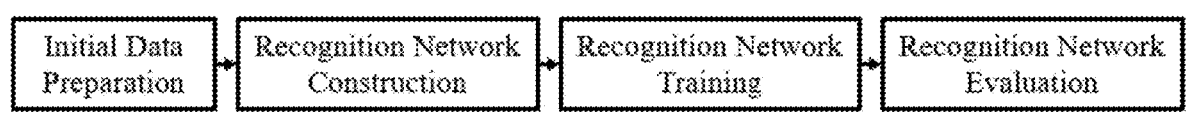
FIG. 1 is a specific implementation flowchart.

The present invention proposes a deep network lung texture recognition method combined with multi-scale attention. The detailed description with reference to the drawings and embodiments is as follows:

The invention constructs a recognition network, uses the convolution and residual modules to construct the basic network, uses the multi-scale feature fusion module to learn the multi-scale feature information contained in the lung texture, and uses the attention mechanism module to automatically filter the feature information that are beneficial to the recognition task, and automatically suppress feature information that is weakly related to the recognition task. The use of CT lung texture image patches for training has achieved a high recognition accuracy in the test. The specific implementation process is shown in FIG. 1, and the method includes the following steps;

1) Initial data preparation: The initial data includes lung texture CT image patches and corresponding class labels for training and testing.

1-1) Collect several examples of CT images with 7 typical lung textures. These 7 lung textures are consolidation, honeycombing, nodular, emphysema, ground glass opacity, reticular ground glass opacity and normal texture.

1-2) Invite radiology experts to manually label the 7 typical textures on the collected CT images, that is, select the coronary slices containing the typical textures in the CT images, and manually outline the typical area of 7 textures in these slice.

Figure 2:
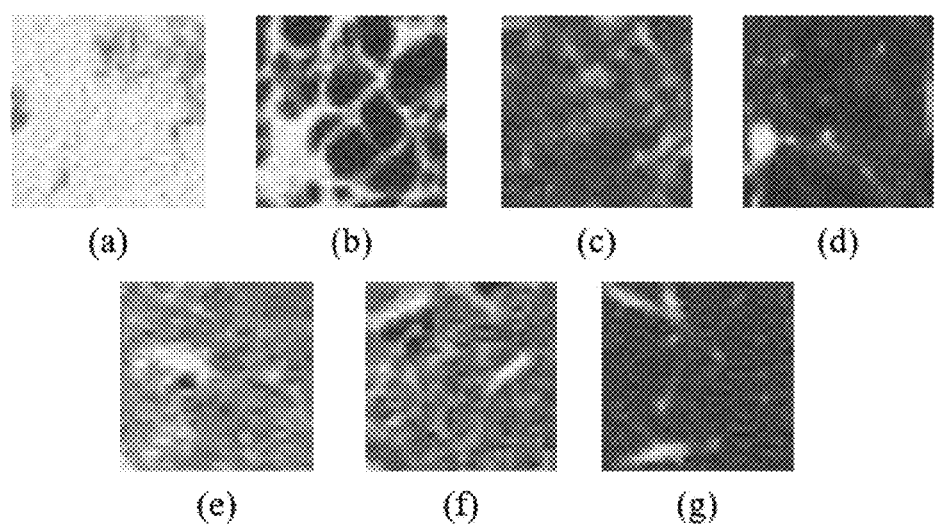
FIG. 2 is a sample image of 7 types of CT lung texture image patches, where (a) consolidation; (b) honeycombing; (c) nodular; (d) emphysema; (e) ground glass opacity; f) reticular ground glass opacity; (g) normal.

1-3) For the area labeled in 1-2), use a square frame with a size of 32×32, randomly intercept small patches of CT images, and combine the labeling information of experts, and finally generate a number of 32×32 with labels (texture category) CT image patches. FIG. 2 is a sample diagram of 32×32 CT small patches intercepted for various types of marked textures. These labeled CT image patches will be used for training and testing the method of the present invention.

Figure 3:
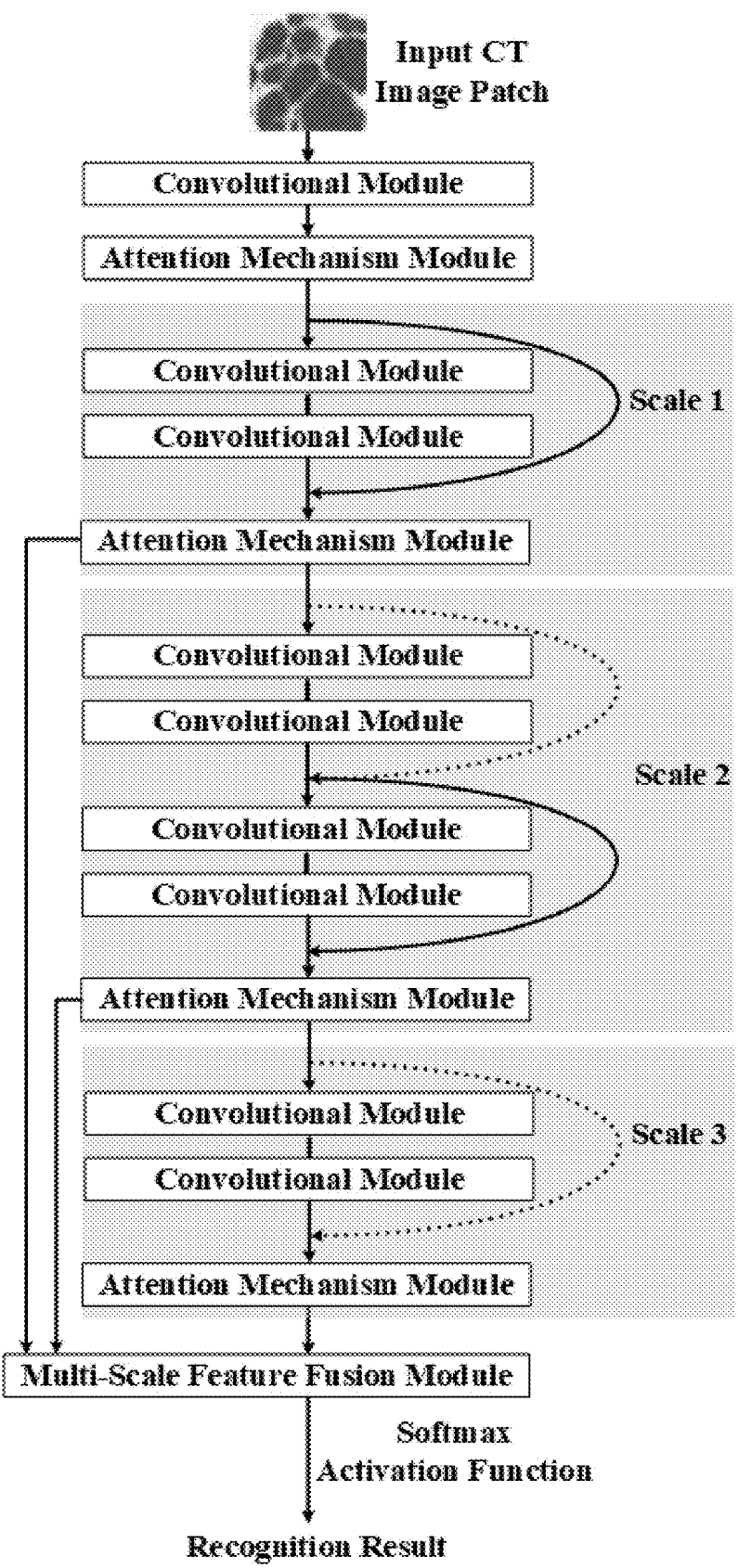
FIG. 3 is a diagram of the recognition network structure.

2) Construction of recognition network: construct basic network with convolution and residual modules, use multi-scale feature fusion module to learn multi-scale feature information of lung texture, and use attention mechanism module to filter features that are beneficial to recognition while suppressing features that have weaker relationship with recognition and ultimately improve the recognition accuracy. FIG. 3 is a diagram of the identification network structure.

Figure 4:
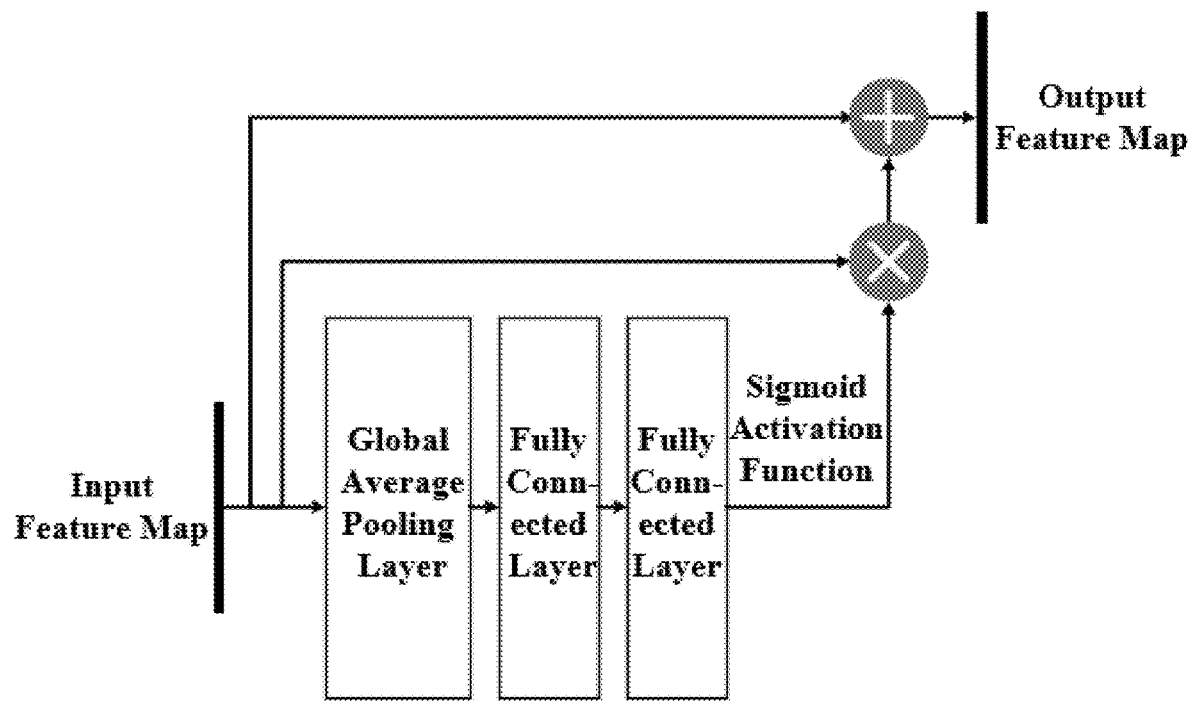
FIG. 4 is a structural diagram of the attention mechanism module.
Figure 5:
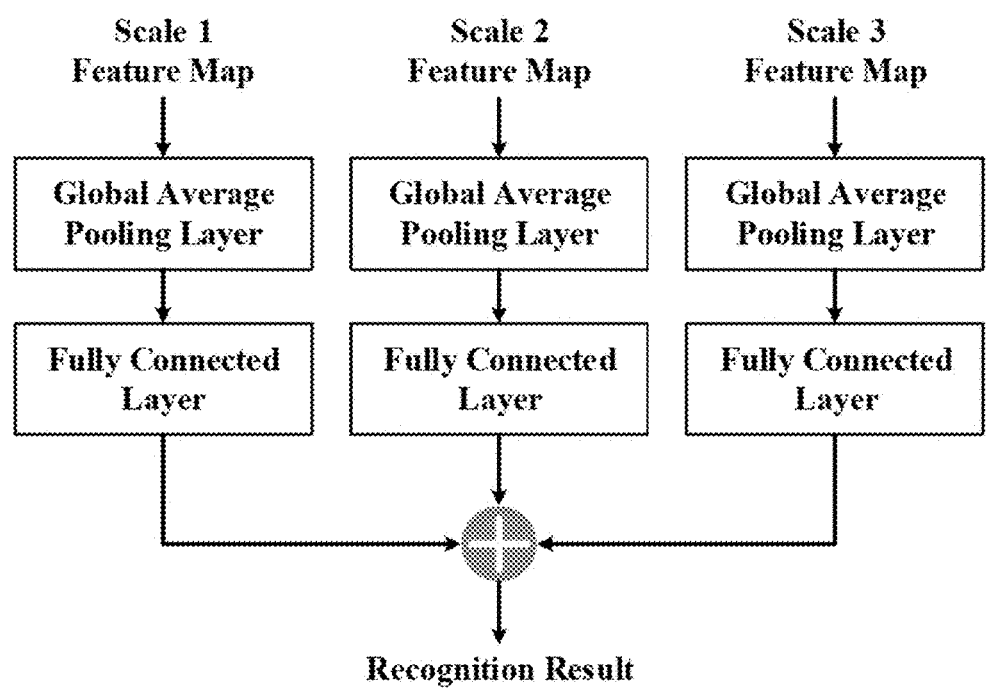
FIG. 5 is a structural diagram of a multi-scale feature fusion module.

2-1) The recognition network is composed of basic network, attention mechanism module and multi-scale feature fusion module. The basic network consists of 9 convolution modules, which learn feature information from the input CT lung texture image patches at three different scales. The feature information learned at each scale automatically filters the feature information that is beneficial to the recognition task through the attention mechanism module, and automatically suppresses the feature information that is weakly related to the recognition task. The feature information learned by the three scales is finally fused through the multi-scale feature fusion module, and the recognition results are given;

2-2) Each convolution module consists of general units of deep neural network, namely convolution layer, batch normalization layer and rectified linear unit layer. The convolution kernels of all convolutional layers are set to 3. The number of convolution channels of the 1-3th convolution module is set to 128, the number of convolution channels of the 4-7th convolution module is set to 256, and the number of convolution channels of the 8-9th convolution module is set to 512;

2-3) Except for the first convolution module, the remaining 8 convolution modules, every two of them is a group connected by jump connection to form a total of 4 residual modules. For a residual module (Kaiming He, Xiangyu Zhang, and et. al., "Deep residual learning for image recognition," in Computer Vision and Pattern Recognition, 2016, pp. 770-778.), the input is through internal convolution modules to learn new feature information, and the jump connection connects the input of the residual module with the feature map learned by the internal second convolution module to form a residual learning mechanism. By introducing a residual learning mechanism, the problems of gradient disappearance and gradient explosion that are easy to occur during neural network training are avoided, and the network learning efficiency is improved. When the input of the residual module and the output data matrix of the second internal convolution module have the same size, the jump connection is an identity map, that is, the two are directly added together. Otherwise, the jump connection is a convolutional layer, the convolution kernel size is set to 1, the convolution stride is set to 2, and the input feature map of the residual module is adjusted to be the same size as the output data matrix of the second internal convolution module;

2-4) The four residual modules learn multi-scale feature information from the input CT lung texture image patches at three different scales according to the ratio of 1:2:1. The convolutional layer of the first convolution module in the second and third scales has a convolutional stride of 2, which achieves a 2 times down sampling of the input feature map and reduces the input feature map resolution, expand the local receptive field of the convolution module to increase the scale. The convolutional stride of the other convolutional layers are set to 1, keeping the resolution of the input feature map and the output feature map consistent to maintain the scale;

2-5) The convolution module at the beginning of the network and the last residual module in 3 scales are all connected with an attention mechanism module, which is used to automatically filter the feature information learned by the convolution module or the residual module that is beneficial to the recognition task, while automatically suppress feature information that has a weak relationship with the recognition task. FIG. 4 is a structural diagram of the attention mechanism module. The input feature map first calculates the average value of the feature map through the global average pooling (GAP) layer in units of channels. The resulting vector connects 2 fully connected layers, of which the number of neurons in the first fully connected layer is 0.5 times of the number of elements in the input vector, the number of neurons in the second fully connected layer is the same as the number of elements in the input vector, and then the activation vector is obtained through the Sigmoid activation function. The activation vector and the input feature map are multiplied according to the channel to obtain a weighted feature map. The weighted feature map is then added to the input feature map to form a residual learning mechanism to improve the learning efficiency of the attention mechanism module. The result is the output of the attention mechanism module. The global average pooling and Sigmoid activation function used here are general modules in deep networks;

2-6) The multi-scale feature fusion module is used to fuse the feature information learned at three scales and give the recognition results. FIG. 5 is the structure diagram of multi-scale feature fusion module. The module contains 3 branches, and the feature information learned at the corresponding scale is used as input. The average value of the feature map is calculated in units of channels through the GAP layer, and then a fully connected layer containing 7 neurons is connected, and the reason why the number of neurons is 7 is that the present invention is used to identify 7 typical textures of diffuse lung diseases. The vectors generated by the fully connected layers of the three branches are added correspondingly and the recognition result is obtained through the Softmax activation function. The Softmax activation function here is a general module in the deep network.

3) Train based on the recognition network obtained in step (2).

3-1) Online data augmentation is performed on the CT image patches participating in the training, and the specific forms include random flipping and random translation.

3-2) The recognition network is trained in a small batch using the cross-entropy loss function. The loss function formula is as follows:

$$L(y, y') = -\frac{1}{n}\sum_{x}(y'\log(y))$$

In the formula, $L(\cdot)$ represents the value of the cross-entropy loss function, n represents the number of CT image patches participating in training in a single batch, n is 128 in the present invention, and x represents the data matrix of CT image patches participating in training in a single batch, $\Sigma$ is the summation operator, y' represents the category label matrix corresponding to x, $\log(\cdot)$ represents the logarithmic operation, and y represents the category label matrix of x recognized by the recognition network.

3-3) The stochastic gradient descent algorithm is used to optimize the recognition network using the loss function in step (3-2). The initial value of the learning rate is set to 0.01, and each epoch is updated to 0.97 times the previous epoch. The network optimization process terminates when the validation set recognition accuracy is the highest.

4) Use test data to evaluate network performance. In the performance evaluation, the two commonly used indicators in the recognition experiment are calculated according to the test results, namely the correct recognition accuracy and the F-value. Here not only the performance of the method of the present invention is tested, but also compared with other six lung texture recognition methods. The specific results are shown in Table 1,

TABLE 1

Performance evaluation of the method of the present invention and comparison with other methods

| Method | Accuracy | $F_{avg}$ |
|---|---|---|
| (a) VGG-16 | 0.8663 | 0.8657 |
| (b) ResNet-50 | 0.8766 | 0.8795 |
| (c) LeNet-5 | 0.8799 | 0.8822 |

TABLE 1-continued

Performance evaluation of the method of the present
invention and comparison with other methods

| Method | Accuracy | $F_{avg}$ |
|---|---|---|
| (d) CNN-5 | 0.9144 | 0.9080 |
| (e) Bag-of-Feature | 0.9251 | 0.9227 |
| (f) DB-ResNet | 0.9352 | 0.9334 |
| (g) MSAN | 0.9478 | 0.9475 |

Among them (a) is the correct recognition accuracy and F-value of deep convolutional neural network (VGG-16) (K. Simonyan and A. Zisserman, "Very deep convolutional networks for large-scale image recognition", Computer Science, 2014.); (b) is the correct recognition accuracy and F-value of residual network (ResNet-50) (K. He and et al., "Identity mappings in deep residual networks," in European Conference on Computer Vision, 2016, pp. 630-645.); (c) is the correct recognition accuracy and F-value of LeNet-5 (Y. Lecun, L. Bottou, Y. Bengio, and P. Haffner, "Gradient-based learning applied to document recognition," Proceedings of the IEEE, vol. 86, no. 11, pp. 2278-2324, 1998.); (d) is the correct recognition accuracy and F-value of 5-layer convolutional neural network (CNN-5) (M. Anthimopoulos, S. Christodoulidis, and et. al., "Lung pattern classification for interstitial lung diseases using a deep convolutional neural network," IEEE Transactions on Medical Imaging, vol. 35, no. 5, pp. 1207-1216, 2016.); (e) is the correct recognition accuracy and F-value of bag-of-feature-based method (Bag-of-Feature) (R. Xu, Y. Hirano, R. Tachibana, and S. Kido, "Classification of diffuse lung disease patterns on high-resolution computed tomography by a bag of words approach," in International Conference on Medical Image Computing & Computer-assisted Intervention (MICCAI), 2011, p. 183.); (f) is the correct recognition accuracy and F-value of dual-branch residual network (DB-ResNet) (R. Xu and et al., "Pulmonary textures classification using a deep neural network with appearance and geometry cues," in IEEE International Conference on Acoustics, Speech and Signal Processing (ICASSP), 2018.); (g) is the correct recognition accuracy and F-value of the method of the present invention (MSAN).

The invention claimed is:

1. A deep network lung texture recognition method combined with multi-scale attention, wherein including the following steps:
 1) Initial data preparation: initial data includes lung texture CT image patches and corresponding class labels for training and testing;
 2) recognition network construction: use convolution and residual modules to construct a basic network, use a multi-scale feature fusion module to learn a multi-scale feature information of a lung texture, and use a attention mechanism module to automatically filter feature maps, and ultimately improve recognition accuracy;
 3) recognition network training: training based on the recognition network obtained in step (2);
 4) use test data to evaluate network performance;
 wherein structure of the recognition network constructed in step 2) specifically including the following steps:
 2-1) the recognition network is composed of the basic network, the attention mechanism module and the multi-scale feature fusion module; the basic network learns the feature information from input CT lung texture image patches at different scales; the feature information learned at each scale automatically filters the feature information that is beneficial to a recognition task through the attention mechanism module, and automatically suppresses the feature information that has weaker relationship with the recognition task; the feature information learned at different scales is finally fused by the multi-scale feature fusion module, and recognition results are given;
 2-2) the network contains convolution modules, each of the convolution modules is composed of general units of deep neural network, that is, convolution layer, batch normalization layer, and rectified linear unit layer; the convolution modules are connected by jump connections to form residual modules, which improves efficiency of feature learning by introducing residual learning mechanism;
 2-3) the network contains the attention mechanism modules, which are used to automatically filter the feature information that is beneficial to the recognition task from the feature information learned by the convolution module or the residual module, and automatically suppress the feature information that is weakly related to the recognition task;
 2-4) the feature information learned by the network at different scales is effectively fused through the multi-scale feature fusion module, and the recognition results are given.

2. The deep network lung texture recognition method combined with multi-scale attention according to claim 1, wherein the structure of the recognition network constructed in step 2), in combination with the embodiment, specifically includes the following steps:
 2-1) the recognition network is composed of the basic network, the attention mechanism module and the multi-scale feature fusion module; the basic network is composed of 9 convolution modules, and learns the feature information from the input CT lung texture image patches at three different scales; the feature information learned at each scale is automatically filtered through the attention mechanism module for the feature information that is beneficial to the recognition task, and at the same time, automatically suppresses the feature information that has a weak relationship with the recognition task; the feature information learned by the three scales is finally fused through the multi-scale feature fusion module, and the recognition results are given;
 2-2) each of the convolution modules is composed of general units of deep neural network, namely the convolution layer, the batch normalization layer and the rectified linear unit layer; a convolution kernel of the convolution layers is set to 3; a number of convolution channels of 1-3th convolution module is set to 128, the number of the convolution channels of the 4-7th convolution module is set to 256, and the number of convolution channels of 8 9th convolution module is set to 512;
 2-3) except for first convolution module, remaining 8 convolution modules, every two of which is a group connected by jump connections to constitute a total of 4 residual modules; an input off a residual module is passed through internal convolution modules to learn new feature information, and the jump connection connects the input of the residual module to the feature map learned by an internal second convolution module to form a residual learning mechanism; when a size of data matrix of input of the residual module and an output of the internal second convolution module are identical, the jump connection is an identity map, that is, the two are directly added; otherwise, the jump connection is a convolution layer, the size of the convolution kernel is set to 1, the convolution stride is set to 2, the output feature maps of residual module is adjusted to have a same size as the output data matrix of the second internal convolution module;

2-4) the four residual modules learn multi-scale feature information from an input CT lung texture image patches at three different scales according to a ratio of 1:2:1; a convolution stride of first convolution layer of first convolution module in the second and third scales is set to 2 to achieve 2 times down sampling of the input feature map, reduce a resolution of the input feature map, and expand the local receptive filed of convolution module to increase scale; the convolutional strides of the other convolutional layers are all set to 1, keep the resolution of the input feature map and the output feature map consistent to maintain the scale;

2-5) the convolution module at the beginning of the network and the last residual module in 3 scales are all connected with an attention mechanism module, which is used to automatically filter the feature information learned by the convolution module or the residual module that is useful for recognition tasks and automatically suppresses feature information that is weakly related to the recognition task; input feature maps first calculate an average of the feature maps in units of channels through a global average pooling layer, and the resulting vector connects 2 fully connected layers, where a number of neurons in the first fully connected layer is 0.5 times of a number of elements in the input vector, the number of neurons in the second fully connected layer is identical to the number of elements in the input vector, and then the activation vector is obtained through the Sigmoid activation function; the activation vector is multiplied with input feature maps by the channel correspondence to obtain a weighted feature map; the weighted feature map is then added to the input feature map to form the residual learning mechanism to improve the learning efficiency of the attention mechanism module; the result is used as an output of the attention mechanism module;

2-6) the multi-scale feature fusion module is used to fuse the feature information learned at the three scales and give the recognition results; the module contains 3 branches, takes the feature information learned at the corresponding scale as input, and calculate a mean value of feature maps in units of channels through global average pooling layer, and then a fully connected layer containing 7 neurons is connected, the vectors generated by the three-branch fully connected layers are added correspondingly and the recognition result is obtained through a Softmax activation function.

* * * * *